United States Patent [19]

Kohsaka et al.

[11] Patent Number: 4,761,074
[45] Date of Patent: Aug. 2, 1988

[54] METHOD FOR MEASURING IMPURITY CONCENTRATIONS IN A LIQUID AND AN APPARATUS THEREFOR

[75] Inventors: Yasuo Kohsaka, Sakai; Tohru Niida, Minoo; Hisao Sato, Sagamihara; Hajime Kano, Suita, all of Japan

[73] Assignees: Nihon Kagaku Kogyo Co., Ltd., Osaka; Nomura Micro Science Co., Ltd., Tokyo, both of Japan

[21] Appl. No.: 29,635

[22] Filed: Mar. 24, 1987

[30] Foreign Application Priority Data

Mar. 24, 1986 [JP] Japan .................................. 61-66683

[51] Int. Cl.⁴ ...................... G01N 21/01; G01N 21/85
[52] U.S. Cl. ...................... 356/37; 356/336; 356/338
[58] Field of Search ................ 356/37, 336, 338; 250/222.2

[56] References Cited

U.S. PATENT DOCUMENTS 4,449,816  5/1984  Kohsaka et al.

FOREIGN PATENT DOCUMENTS 266490 11/1965 Australia ............................. 356/37

Primary Examiner—Davis L. Willis
Assistant Examiner—Matthew W. Koren
Attorney, Agent, or Firm—Lowe, Price, Leblanc, Becker & Shur

[57] ABSTRACT

A method and an apparatus for measuring an impurity concentration of a liquid comprises atomizing step for atomizing the objective liquid, e.g. pure water, having a predetermined droplet size distribution, and an evaporating step for evaporating to dryness the droplets so as to generate fine particles. Those particles are fed to a condensation nuclei counter, hereinafter referred to as CNC, which counts the number of fine particles and has a specified sensitivity characteristic curve. Then impurity concentration of the objective liquid can be measured, since the concentration is related to the counted number of the CNC, the distribution of droplet size of the atomizer, and the sensitivity characteristic of the CNC including the particle deposition loss.

16 Claims, 2 Drawing Sheets

METHOD FOR MEASURING IMPURITY CONCENTRATIONS IN A LIQUID AND AN APPARATUS THEREFOR

BACKGROUND OF THE INVENTION (1) Field of the Invention

The present invention relates to a method of measuring low concentration of impurity in a high pure liquid such as high pure water, and a measuring apparatus therefor.

(2) Prior Art

Cleaning processes are employed in semiconductor manufacturing processes, especially in wafer processing of very large scale integrated (hereinafter referred to as VLSI) circuits. Such a process requires water of high purity. In case water includes a small amount of fine particles, microorganism, or non-volatile solute, such impurities substances come out on rinsed wafers, and they cause defects of minute patterns. Therefore, improvement of the purity of high pure water is required in order to improve yield of VLSI semiconductor devices.

In this connection, a measuring apparatus which can measure a concentration of particles or impurities in pure high water in high sensitivity has been required. One conventional measuring method includes a filtering step in which objective pure water is filtered by a filter, and a counting step in which number of particles on the filter is counted by an electron microscope. Another conventional method includes an evaporating step in which the objective water is evaporated and a measuring step in which impurity concentration of the water is measured by weighing dried remains.

However, since it takes a long time to measure the purity of pure water by such conventional methods, it is impossible to manufacture the pure water and to count the number of particles simultaneously. Furthermore, there is a shortcoming in that much manual skill is necessary.

Another conventional measuring apparatus is provided with a laser light source projected in the objective liquid, a light detecting means which detects light scattered by particles passing through a measuring region, and a signal processing means which counts photoelectric converted pulse trains. The apparatus can measure the number of particles or sizes. However, a high power laser light source such as argon ion laser is necessary for counting the number of fine particles by such a light scattering method. This results in the apparatus of large size. In addition, the range of particle size of these measurements is limited to e.g. above 0.1 $\mu$m, and it is impossible to detect particles of smaller size, or impurities dissolved in a liquid.

Another conventional measuring apparatus is provided with an atomizer for atomizing an objective liquid by hot clean air and evaporating minute droplets, an optical means which irradiates floating impurities and detects scattered light, and a measuring means which measures both the number of particles and the particle sizes. However, the size range of this measurement is also limited to e.g. above 0.1 $\mu$m. The lowest limitation of the measurement of concentration of impurities dissolved in high pure water is also about several 10 PPB ($10 \times 10^{-9}$). It is practically necessary to measure impurity concentration in high pure water lower than that value.

SUMMARY OF THE INVENTION

The present invention overcomes such disadvantages of the conventional apparatus mentioned above, and provides a method and an apparatus for measuring an extremely low concentration of minute impurities totally dissolved in a pure liquid, such as pure water.

DESCRIPTION OF THE PREFERRED EMBODIMENT

The present invention relates to a method for measuring impurity concentration of an objective liquid and an apparatus therefor. The method comprises the steps of an atomizing step in which the objective liquid is mixed with clean air so that fine droplets having a predetermined size distribution are generated, an evaporating step in which the fine droplets are evaporated to dryness and non-volatile fine particles are produced, a size enlarging step in which vapor is condensed on the fine particles as nuclei so that the sizes of the fine particles are enlarged, a counting step for optically counting the number of the enlarged fine particles, and a data processing step for processing data based on the sensitivity characteristic of the optical detection in the counting step, distribution of the droplet size in the atomizing step, and the counted value in the counting step. And the apparatus comprises an atomizer for atomizing the objective liquid by mixing with clean air and generating fine droplets having a predetermined size distribution, an evaporator for evaporating to dryness the fine droplets and generating non-volatile fine particles, a condensation nuclei counter for counting the number of the fine particles, and a signal processing means for processing the impurity concentration of the objective liquid based on the sensitivity characteristic of the condensation nuclei counter, the distribution of the droplet size of the atomizer, and the counted value of the condensation nuclei counter.

Figure 1:
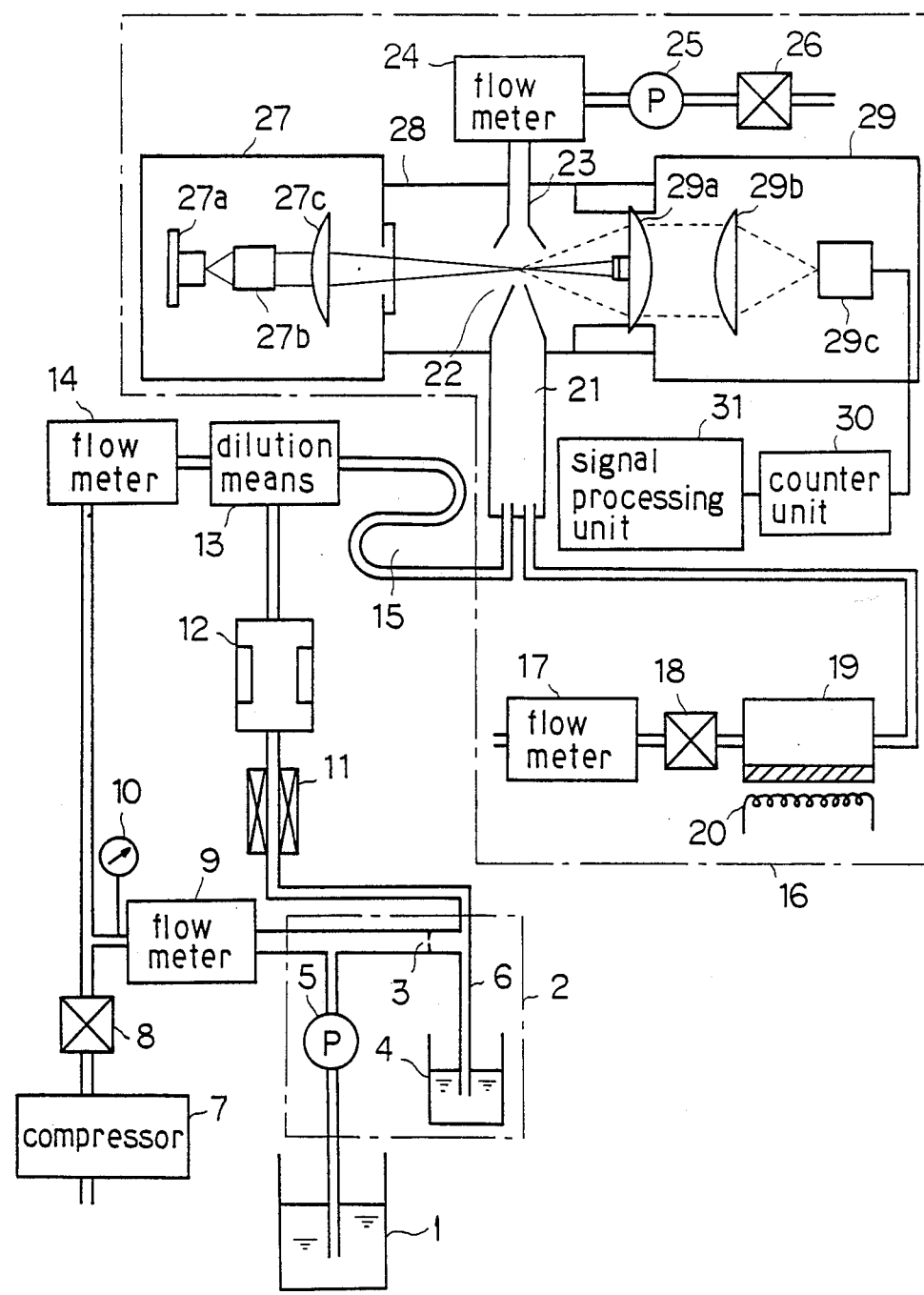
FIG. 1 is a block diagram of an impurity concentration measuring apparatus embodying the present invention.

The preferred embodiment of the present invention will be described below, by referring to the block diagram of FIG. 1. In this figure, a vessel 1 contains pure water which is an objective liquid. Water in the vessel 1 is fed constantly to an atomizer 2. The atomizer 2 has a nozzle 3, a vessel 4, and a quantitative pump 5 which feeds pure water of the vessel 1 to the nozzle 3. A drain duct 6 is connected to the nozzle 3 and the vessel 4. A compressor 7 feeds clean high pressure air to the nozzle 3 of the atomizer 2 through a filter 8 and a flow meter 9. A pressure meter 10 is connected to the duct between the filter 8 and the flow meter 9. Pure water and compressed air are fed into the nozzle 3 so that the atomizer 2 atomizes the pure water and generates vapor, including a great number of fine droplets having a predetermined mean value and a distribution of droplets size. The rest of the water is drained to the vessel 4 through the drain duct 6. The vapor is fed into an evaporator 11.

The evaporator 11 leads the fine droplets into a metal duct heated approximately at 60°-70° C. and evaporates the droplets immediately. As a result of this, the evaporator 11 generates aerosol including ultrafine particles, sizes thereof being fixed by the sizes of the droplets generated by the atomizer 2 and by the purity of the water. The aerosol is fed to a charge remover 12. The charge remover 12 removes charges from the ultrafine particles by an irradiation of radiant rays or an application of corona discharge, and feeds the aerosol to a dilution means 13. The compressor 7 also feeds clean air to the dilution means 13 through the filter 8 and a flow meter 14. The dilution means 13 dilutes the aerosol with clean air at a predetermined rate, then feeds a part of the diluted aerosol to a filter 15, and exhausts the rest. The filter 15 is, e.g. a metal pipe having a predetermined inner diameter, and removes ultrafine particles having sizes below a specified size. The ultrafine particles stick to the inner wall of the filter 15 because of the Brownian movement. Then the aerosol without the ultrafine particles is fed to a condensation nuclei counter 16, which is hereinafter referred to as CNC.

As described in U.S. Pat. No. 4,449,816, issued May 22, 1984 to Kohsaka et al., the CNC 16 condenses some appropriate vapor on the aerosol particles as nuclei, and enlarges the particle sizes so that it is possible to observe optically and to count the number of the particles. The CNC 16 has a flow meter 17 and a filter 18 as shown in FIG. 1. The inlet of the flow meter 17 is open to the air, and the outlet thereof is connected to a high temperature saturated vapor chamber 19 through the filter 18. The chamber 19 includes a solvent such as water heated by a heater 20, and feeds saturated high temperature vapor to a mixing chamber 21. The aerosol including fine particles passing through the filter 15 is also fed to the mixing chamber 21. The mixing chamber 21 is a chamber in which the aerosol of normal temperature and the clean saturated high temperature vapor are mixed. Thus, the vapor is condensed on the fine particles as nuclei. As a result of this, the fine particles are magnified to be optically observed. An outlet of the mixing chamber 21 is formed as a nozzle 22. The mixing chamber 21 is fixed so that the top of the nozzle 22 faces to an exhaust duct 23 across which light rays pass. The inlet of the exhaust duct 23 inhales the exhausted aerosol from the nozzle 22. The other end of the exhaust duct 23 is connected to a flow meter 24. An outlet of the flow meter 24 is connected to a pump 25. The pump 25 inhales the exhausted gas and releases the air through a filter 26, so as to jet the aerosol from the nozzle 22.

The CNC 16 further comprises an optical measuring means which optically detects the number of the fine particles in the aerosol. The optical measuring means has a light source chamber 27, a measuring chamber 28, and a detecting chamber 29. The light source chamber 27 has a laser light source 27a such as a laser diode, and focusing lenses 27b and 27c. The laser beam from the light source 27a is focused at a measuring region which is between the ducts 22 and 23 in the measuring chamber 28. The aerosol flow perpendicularly confronts the laser light, and therefore the particles of the aerosol scatter the laser light. The measuring chamber 28 has an airtight structure in order to keep the particle size and to reduce noise due to unexpected light. The detecting chamber 29 has collecting lenses 29a and 29b and a photoelectric transducer 29c. The collecting lenses 29a and 29b collect the scattered light at the photoelectric transducer 29c, which converts the light intensity to an electric signal. The signal of the photoelectric transducer 29c is applied to a counter unit 30 of the CNC 16. The counter unit 30 counts the number of pulses from the photoelectric transducer 29c, and the counted data is transferred to a signal processing unit 31. The signal processing unit 31 measures the purity of the pure water in the vessel 1 based on the distribution of the droplet size of the atomizer 2, a limit of measurement of the particle size of the CNC 16 and the counted value of the counter unit 30.

Figure 2:
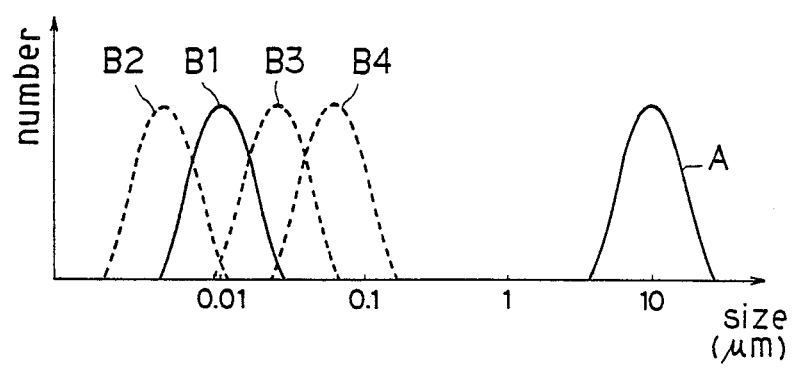
FIG. 2 shows a distribution of droplet size immediately after an atomization (curve A) and distributions of particle sizes immediately after an evaporation to dryness (curves B1 to B4).

Next, the principle of the purity measurement of the present invention is mentioned in detail below. The distribution of the droplet size of the pure water, immediately after the atomization by the atomizer 2 is a specified distribution, e.g. a logarithm normal distribution. In the present embodiment, the mean value of the particle size of the atomizer 2 is a specified value, e.g. 10 μm as a curve A as shown in FIG. 2. The evaporator 11 evaporates the atomized droplets without any treatment, then the distribution of the educed fine particle size shifts to the left as a curve B1 but keeps its shape of the logarithm normal distribution as shown in FIG. 2. The mean particle size of the evaporator 11 depends on the purity of the pure water. If the purity of the water is higher, then the distribution of the educed particle shifts to the left further shown as a dotted line B2, and if the purity thereof is lower, the distribution does not shift left so much shown as a dotted line B3 or B4 of FIG. 2. However, the shape of the distribution and the number of the particles are the same as those of the original atomized droplets.

Figure 3:
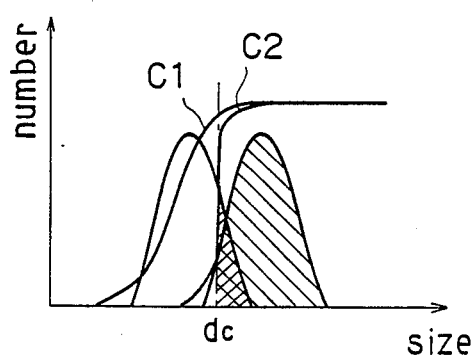
FIG. 3 is a graph showing size distributions of different concentrations and a sensitivity characteristic curve of a condensation nuclei counter.

On the other hand, although the counter unit 30 of the CNC 16 counts the number of fine particles, it is not able to count the number of the ultrafine particles under specified size. The detective sensitivity of the CNC 16 for the ultrafine particle reduces gradually under that specified size, and the CNC 16 can count the number of particles having size larger than that size in safe. In the present embodiment, since the aerosol of the dilution means 13 is fed to the CNC 16 through the filter 15, ultrafine particles having size below the specified size stick to the inner wall of the filter 15, so that such particles are not fed to the CNC 16. Therefore, in case the cut-off particle size of the filter 15 is selected above the changing point of the CNC 16, the sensitivity characteristic curve of the CNC 16 including the filter 15 changes the curve C1 into a curve C2 as shown in FIG. 3. As a result of this, the changing point of the sensitivity characteristic becomes sharp and the lower limit size of the detection is determined by "$d_c$". Then the particle number detected by the CNC 16 depends on the purity of the water, in a region where the skirt part of the distribution curve B1, B2, B3 or B4 and the sensitivity characteristic of the CNC 16 including the filter 15 overlap with each other. Therefore, the purity is known by the counted value of the CNC 16. In case the distribution function of the particle size dv of the non-volatile impurities is shown as $P(d_v)$, the particle number N of the CNC 16 is given as follows;

$$N = \int_{d_c}^{\infty} p(d_v)dd_v. \tag{1}$$

If a particle size immediately after the atomization is $d_a$, a size $d_v$ of an educed particle is given as follows;

$$d_v = kd_a C^{\frac{1}{3}} \tag{2},$$

where k usually equals to the value of 1 when the evaporator 11 evaporates the fed water completely or else it is a constant value which depends on the evaporator 11, and C is an impurity concentration of the objective water.

Therefore, the impurity concentration C of the pure water can be obtained based on the number N of the counter unit 30 of the CNC 16 and the distribution function $P(d_a)$ of the distribution immediately after the atomization. In other words, the impurity concentration C of the pure water is shown as follows;

$$C = f\{N, d_c, P(d_a)\} \qquad (3),$$

where $d_c$ is a constant number based on the filter 15 and the CNC 16, and $P(d_a)$ is a constant based on the atomizer 2. As a result of this, the impurity concentration C of the pure water is calculated by the number N. For example, in case that the sensitivity characteristic curve of the CNC 16 including the filter 15 has a sharp cut-off characteristic shown as the curve C2 in FIG. 3 and that the droplets generated by the atomizer 2 have a logarithm normal distribution, in which the geometrical standard deviation is designated as $\sigma_a$, the geometrical mean diameter of droplets is designated as $d_a$, and they number of the droplets atomized by the atomizer 2 is designated as $N_o$, and that all of the droplets are fed to the filter 15, then the counted number N with respect to the concentration C is given as follows;

$$N = N_o/2(1 - erf(x)) \qquad (4),$$

where $$x = \frac{\ln(d_c/(d_a C^{\frac{1}{3}}))}{\sqrt{2\ln\sigma_a}}.$$

For example, in case that the particle size $d_c$ of the measurement limitation of the CNC 16 is 0.01 μm, that the mean size of the distribution function $P(d_a)$ of the atomizer 2 is 10 μm, and that the proportional constant k of the above mentioned equation (2) is 1, then the skirt region of the distribution function $P(d_a)$, the center thereof is $10^{-9}$, i.e. 1 PPB can be measured.

If the impurity concentration of the objective water is enough low, e.g. below 100 PPB, the solid impurity size becomes too small, e.g. below 0.1 μm to count its number by the light scattering method directly. However, the number of the particles can be measured by the CNC. The method and the apparatus of the present invention apply this technique to measure impurity concentration of the liquid, especially extremely low impurity concentration.

In the present embodiment, although the apparatus is provided with the metal pipe as the filter 15 in order that the measurable lower limit of particle size $d_c$ becomes constant, many other kinds of filters such as a diffusion battery can be used. Such a filter sharpens the sensitivity curve of the CNC, especially for a low concentration. On the contrary, if the sensitivity curve of the CNC is known, impurity concentration of the liquid can be measured without such a filter. If the detected curve of the CNC 16 including a filter can be shown as $f_c(d_v)$ instead of $d_c$ of the abovementioned embodiment, then the particle number N of the CNC 16 is given as follows;

$$N = \int_0^\infty p(d_v) f_c(d_v) dd_v. \qquad (1)'$$

Therefore, the impurity concentration C of the pure water is shown as follows;

$$C = f\{N, f_c(d_v), p(d_a)\} \qquad (3)'.$$

And if the measurable lower limit of the CNC can be extended lower, the method and the apparatus of the present invention is applicable to measure further low impurity concentration of the liquid.

What we claim is:

1. A method for measuring an impurity concentration of an objective liquid comprising the following steps of;
    an atomizing step in which the objective liquid is mixed with clean air so that fine droplets having a predetermined size distribution are generated,
    an evaporating step in which said fine droplets are evaporated to dryness and non-volatile fine particles are produced,
    a size enlarging step in which vapor is condensed on said fine particles as nuclei so that the sizes of said fine particles are enlarged,
    a counting step for optically counting the number of said enlarged fine particles, and
    a data processing step for processing data based on said sensitivity characteristic of the optical detection in said counting step, distribution of said droplet size in said atomizing step, and the counted value in said counting step.

2. A method for measuring an impurity concentration of an objective liquid in accordance with claim 1, wherein said objective liquid is water.

3. A method for measuring an impurity concentration of an objective liquid in accordance with claim 1, wherein said atomizing step generates fine droplets having a logarithm normal distribution.

4. A method for measuring an impurity concentration of an objective liquid in accordance with claim 1, wherein said size enlarging step comprises a first step for removing a part of said fine particles having sizes lower than a predetermined size, and a second step in which vapor is condensed on the rest of said fine particles.

5. A method for measuring an impurity concentration of an objective liquid in accordance with claim 1, wherein said counting step counts the number of particles having sizes up to a predetermined size.

6. A method for measuring an impurity concentration of an objective liquid in accordance with claim 1, wherein said counting step comprises steps of irradiating said enlarged particles, collecting the light scattered by such enlarged fine particles to a photoelectric transducer, and counting the number of a pulses from said photoelectric transducer.

7. A measuring apparatus for measuring the impurity concentration of an objective liquid comprising;
    an atomizer for atomizing said objective liquid by mixing with clean air and generating fine droplets having a predetermined size distribution,
    an evaporator for evaporating to dryness said fine droplets and generating non-volatile fine particles,
    a condensation nuclei counter for counting the number of said fine particles, and a signal processing means for processing the impurity concentration of said objective liquid based on the sensitivity characteristic of said condensation nuclei counter, the distribution of said droplet size of said atomizer, and the counted value of said condensation nuclei counter.

8. A measuring apparatus in accordance with claim 7, wherein said objective liquid is water.

9. A measuring apparatus in accordance with claim 7, wherein said atomizer is for generating fine droplets having a logarithm normal distribution.

10. A measuring apparatus in accordance with claim 7, wherein said condensation nuclei counter comprises,
a mixing chamber means in which a vapor is condensed on said fine particles as nuclei, so that the sizes of said fine particles are enlarged,
an optical means for projecting light beam is projected to said enlarged fine particles and converting light scattered by said particles to electric signal, and
a counting means for counting the number of fine particles passing through said optical means.

11. A measuring apparatus in accordance with claim 10, wherein said condensation nuclei counter further comprises a high temperature saturated vapor chamber for supplying high temperature vapor to said mixing chamber means.

12. A measuring apparatus in accordance with claim 7, wherein said optical means comprises a light source chamber for generating laser light, a measuring chamber for projecting said laser light to said enlarged fine particles, and a detecting chamber for collecting light scattered by said particles to a photoelectric transducer.

13. A measuring apparatus in accordance with claim 12, wherein said filter is a metal pipe in which ultrafine particles having below a specified size stick to the inner wall thereof.

14. A measuring apparatus in accordance with claim 7, wherein said measuring apparatus further comprises a filter means for removing a part of said fine particles of said evaporator having sizes below a specified size, and for supplying the rest of said fine particles to said condensation nuclei counter.

15. A method for measuring an impurity concentration of an objective liquid comprising the following steps of:
an atomizing step in which the objective liquid is atomized so that fine droplets having a predetermined size distribution are generated,
an evaporating step in which said fine droplets are evaporated to dryness and non-volatile fine particles are produced,
a counting step for counting the number of said enlarged fine particles by a condensation nuclei counter, and
a data processing step for processing data based on said sensitivity characteristic of the optical detection in said counting step, distribution of said droplet size in said atomizing step, and the counted value in said counting step.

16. A measuring apparatus for measuring the impurity concentration of an objective liquid comprising:
an atomizer for atomizing said objective liquid and generating fine droplets having a predetermined size distribution,
an evaporator for evaporating to dryness said fine droplets and generating fine particles,
a condensation nuclei counter for counting the number of said fine particles, and
a signal processing means for processing the impurity concentration of said objective liquid based on the sensitivity characteristic of said condensation nuclei counter, the distribution of said droplet size of said atomizer, and the counted value of said condensation nuclei counter.

* * * * *